United States Patent
Hochstein

[11] Patent Number: 6,094,981
[45] Date of Patent: Aug. 1, 2000

[54] CAPACITIVE RAIN SENSOR FOR WINDSHIELD

[75] Inventor: Peter A. Hochstein, Troy, Mich.

[73] Assignee: ITT Automotive Electrical Systems, Inc., Auburn Hills, Mich.

[21] Appl. No.: 09/160,972

[22] Filed: Sep. 25, 1998

[51] Int. Cl.$^7$ .................................................... G01W 1/00
[52] U.S. Cl. ............................................................ 73/170.17
[58] Field of Search .......................... 73/170.17, 170.18, 73/170.19, 170.21, 170.22, 170.23, 335.02, 355.05; 361/286

[56] References Cited

U.S. PATENT DOCUMENTS

| | | |
|---|---|---|
| 4,164,868 | 8/1979 | Suntola . |
| 4,429,343 | 1/1984 | Freud . |
| 4,639,831 | 1/1987 | Iyoda ...................................... 361/286 |
| 4,805,070 | 2/1989 | Koontz et al. ........................... 361/286 |
| 4,827,198 | 5/1989 | Mueller et al. .......................... 318/483 |
| 4,831,493 | 5/1989 | Wilson et al. ........................... 361/286 |
| 5,668,478 | 9/1997 | Buschur ................................ 73/335.02 |
| 5,801,307 | 9/1998 | Netzer ................................... 73/170.17 |

*Primary Examiner*—William Oen
*Attorney, Agent, or Firm*—Howard & Howard

[57] ABSTRACT

The basic windshield assembly 10 is well known and includes an outer layer 12 of glass and an inner layer 18 of glass with a sheet of transparent plastic 24 sandwiched between and bonded to the layers 12 and 18 of glass. A metal oxide coating 26 is disposed between the outer layer 12 of glass and the plastic sheet 24 as well known in the art and is transparent for filtering light, and is also electrically conductive. Accordingly, the assembly 10 is characterized by an isolated section, generally indicated at 28, of the coating 26 being electrically separated from the remainder of the coating 26 for capacitively sensing the presence of moisture on the outer surface 14 of the outer layer 12 of glass. The isolated section 28 of the coating 26 comprises a first plurality of electrodes 30 and a second plurality of electrodes 32, the first 30 and second 32 plurality of electrodes being parallel, interdigitized or interleaved and spaced from one another. The capacitance may detected by a known circuit attached directly to the electrodes 30 and 32 or through a capacitive coupling with the electrodes.

14 Claims, 4 Drawing Sheets

CAPACITIVE RAIN SENSOR FOR WINDSHIELD

BACKGROUND OF THE INVENTION

1. Field of the Invention

The subject invention relates to an automotive windshield assembly including a capacitive circuit to sense the presence of rain drops on the outer surface of the windshield.

2. Description of the Prior Art

Capacitive rain sensing for automotive applications is a relatively well known art as exemplified by numerous U.S. Pat. No. 4,164,868 granted Sep. 21, 79 to Suntola; 4,429,343 granted Jan. 14, 89 to Freud; 4,639,831 granted Jan. 27, 87 to lyoda; 4,805,070 granted Jan. 14, 89 to Koontz et al.; 4,827,198 granted May 2, 89 to Mueller et al.; 4,831,493 granted May 16, 89 to Wilson et al and 5,668,478 granted Sep. 16, 97 to Buschur.

However, in spite of the extent of such rain sensor development, no capacitive sensor has ever been commercially viable. The apparent simplicity of the capacitive approach has been mitigated by many irreducible practical complexities that are only uncovered when the device is field tested.

In essence, all capacitive rain sensors rely upon the dramatically different dielectric constants of water (E=80) and the glass windshield (E=2). An interdigitated capacitor formed on the surface of the windshield or close to the surface of the windshield is commonly employed to detect the presence of water. Capacitance of the water sensing capacitor is typically monitored by means of a high frequency, balanced bridge detector, direct capacity (charge) measurement circuits or by means of radio frequency modulation methods. Common to all of these techniques is the necessity of connecting the measuring circuitry to the water sensing capacitor. Attachment to the sensing capacitor electrodes is one of the critical elements of capacitive water sensing methods that have prevented their use.

In actual practice, the sensing capacitor leads are normally brought out to the edge of the glass surface, where they are connected to the sensing circuitry by means of short leads or clips. Windshield glass is commonly mounted by means of an elastomeric bond to the glass opening, providing a water tight seal. The edge of the windshield is not readily accessible once the glass is mounted, while the proximity of the surrounding metal support structure interferes with the leads that are attached to the glass.

A second problem associated with prior art capacitance sensors is the need for a reasonably large area (typically $10^4$ mm$^2$) which does not interfere with the driver's vision or present an unaesthetic appearance.

This invention applies only to safety, laminated windshield structures which consist of outer and inner glass layers, typically 2 mm thick, separated by a 1 mm, bonded PVB sheet. A typical sensor utilizing the outermost surface of the windshield for detecting rain is disclosed in U.S. Pat. No. 4,827,198(Mueller, et.al) wherein a capacitor is formed on the number one (outer surface) and is directly influenced by water or rain droplets. Coupling to this capacitor is accomplished by means of electrodes buried within the windshield structure, typically located on the number three surface. This '198 patent suggests the use of semitransparent electrodes to perform this coupling function. External connection means are shown which then couple the intermediate electrodes to the sensing circuitry. Aside from the cumbersome lead attachment issue, the use of an exterior water sensing capacitor is troublesome because of contact with the wipers. Extensive experience with such exterior, coated glass shows it to hold up poorly to abrasion. The repeated passage the wiper blade over the sensor to effect "clearing" presents a severe environment to any electrically conductive film deposited on the outer glass surface. Only the most refractive metallic coatings that are sputtered on the glass exhibit the necessary abrasion resistance. However, these films have undesirable high resistivities, and they exhibit different wetting behavior than the surrounding glass yielding uneven wiping patterns. In other instances, as in U.S. Pat. Nos. 4,429,343 (Freud) and 4,639,831 (Iyoda), a plastic coating is applied over the conductive film to protect it from the abrasive wiping action.

The U.S. Pat. No. 4,805,070 (Koontz) discloses a nominally transparent, electrically conductive coating disposed on the outer glass surface to form an interdigitated, water sensing capacitor. Coupling is again provided by similarly transparent, capacitively coupled electrodes which are brought out to the edge of the glass for connections. As noted previously, the use of physically coupled sensing leads is a limitation to the successful implementation of this technology. Lead attachment is always a problem in production, and the fragile nature of the connection precludes long term reliability. Furthermore, any substantial lead length can interfere with effective sensor operation for a variety of reasons: High parasitic capacitance and susceptibility to microphonics (mechanical displacement and /or vibration).

SUMMARY OF THE INVENTION AND ADVANTAGES

A rain sensing windshield assembly comprising an outer layer of glass having a number one outer surface and a number two inner surface, an inner layer of glass having a number three inner surface and a number four interior surface, a sheet of transparent plastic sandwiched between and bonded to the number two and three surfaces of the layers of glass, and an electrically conductive and transparent coating disposed between the plastic sheet and one of the number two and three surfaces of layers of glass. The layers of glass and the plastic sheet and the coating are coextensive to define a windshield periphery. The assembly is characterized by an isolated section of the coating electrically separated from the remainder of the coating for capacitively sensing the presence of moisture on the number one surface of the outer layer of glass.

The invention also includes a method of fabricating the rain sensing windshield assembly comprising the steps of sandwiching a sheet of transparent plastic between and bonded to outer and inner layers of glass, and depositing an electrically conductive and transparent coating between the sheet and one of the layers of glass to be coextensive with the layers of glass and the sheet to define a windshield periphery. The method is characterized by forming an isolated section of the coating electrically separated from the remainder of the coating for capacitively sensing the presence of moisture on the outer layer of glass.

The invention, therefore, provides a capacitive rain sensor which is not subject to the abrasion of the wipers, may be easily electronically coupled and utilizes existing components with little addition to the fabrication method. Since the present invention involves the use of a portion of the existing applied infrared filter coating as a rain sensing detector by electrical isolation of a section of such a coating 26 for rain detection, only a very low incremental cost is incurred to perform a second, desirable function.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
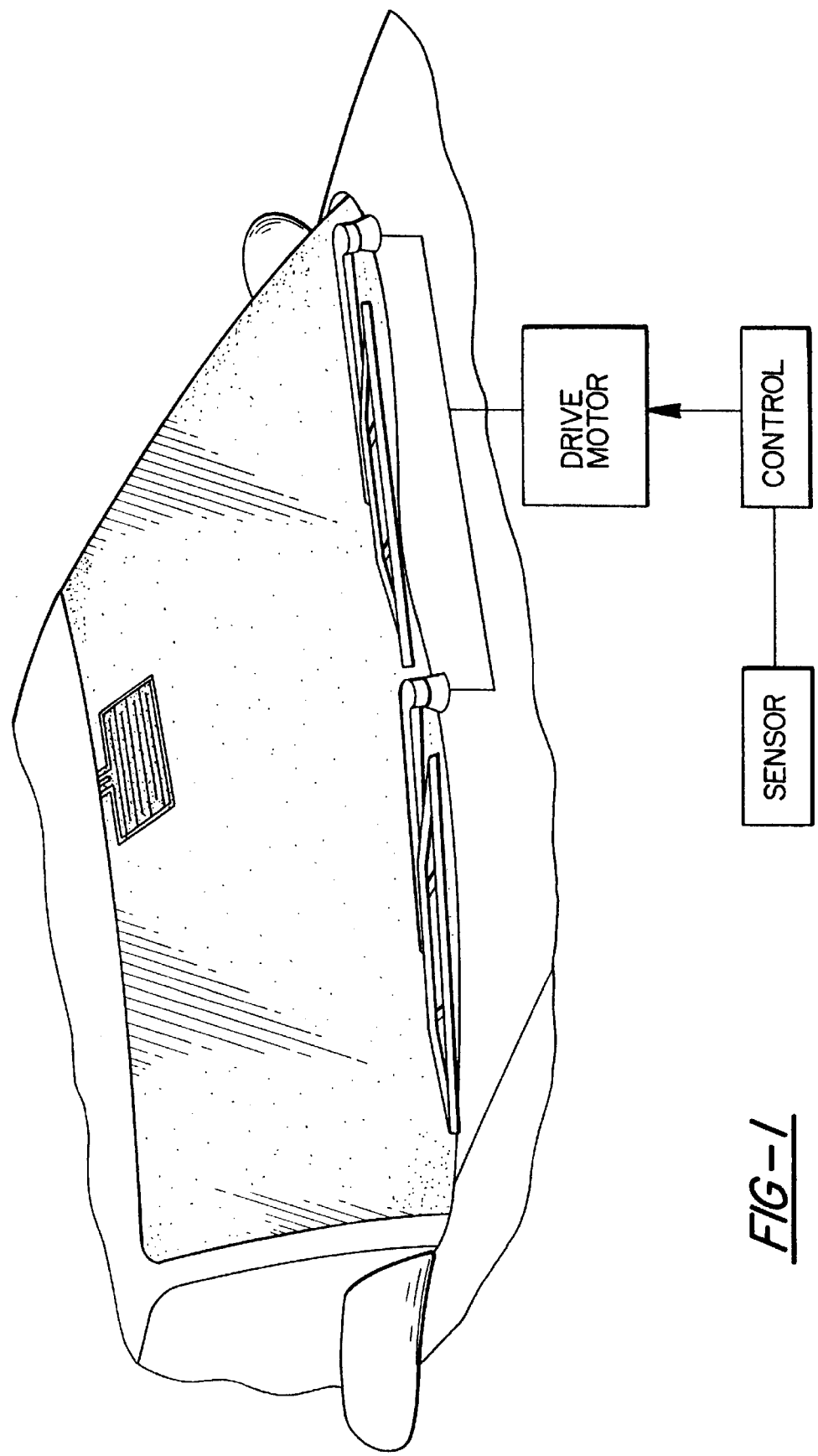
FIG. 1 is a perspective view of a preferred embodiment of the subject invention.

Referring to the Figures, wherein like numerals indicate like or corresponding parts throughout the several views, a rain sensing windshield assembly is generally shown at 10 in FIG. 1. As is well known, the vehicle windshield assembly 10 has moisture removed by wipers which are oscillated by a motor drive. The drive motor is controlled by an electronic control. However, that control actuates the motor in response to moisture on the outside of the windshield, moisture which is sensed by a capacitive sensor as described herein.

Figure 2:
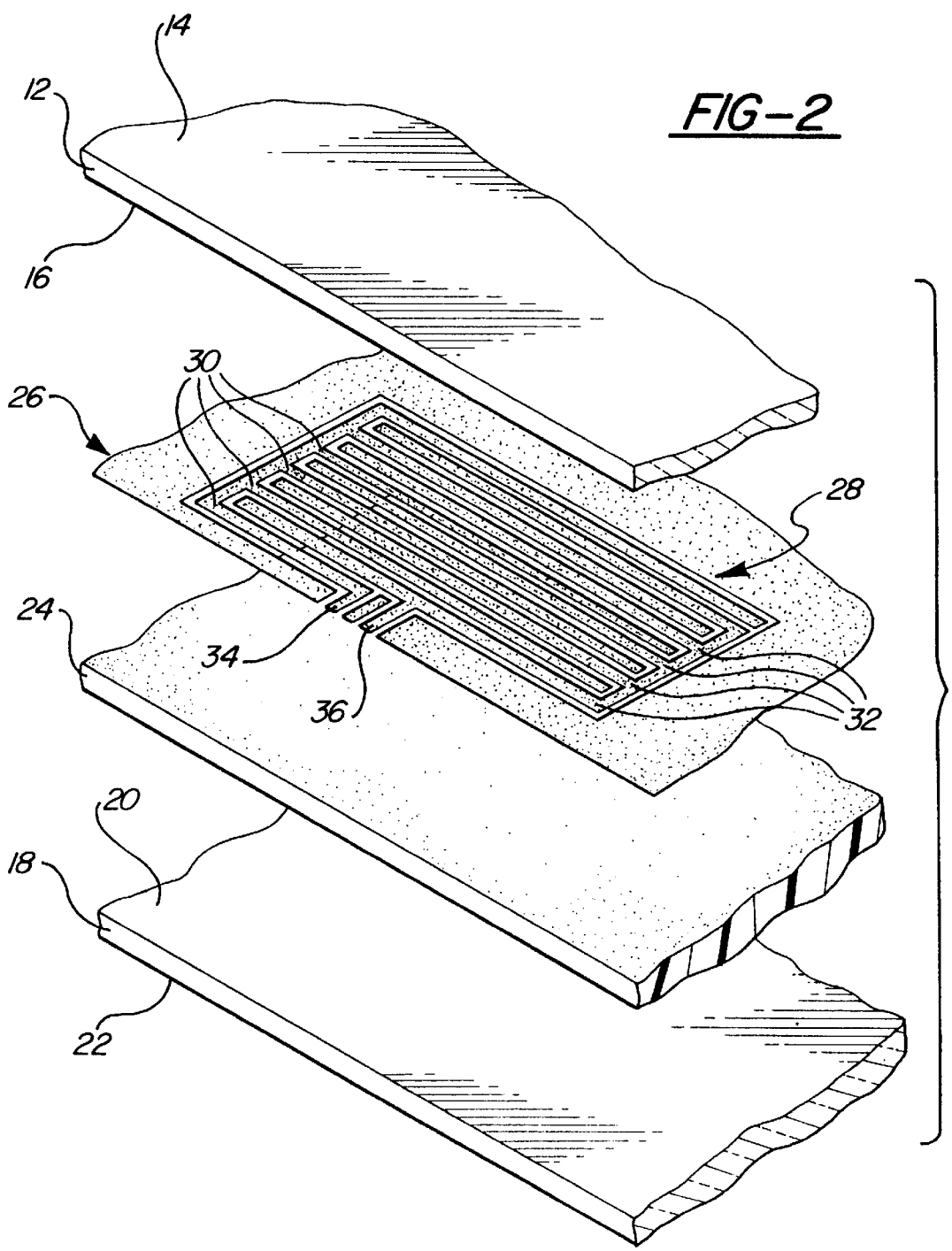
FIG. 2 is a fragmentary, exploded, perspective view of the subject invention.

As shown in FIG. 2, the assembly 10 includes an outer layer 12 of glass having a number one outer surface 14 and a number two interior surface 16 and an inner layer 18 of glass having a number three interior surface 20 and a number four outer surface 22.

A sheet of transparent plastic 24 is sandwiched between and bonded to the number two 16 and three 20 surfaces of the layers 12 and 18 of glass. The sheet of plastic 24 is laminated to the glass layers 12 and 18 as is well known in the art and consists of polyvinylbutyral (PVB), typically 1 millimeter in thickness, the layers 12 18 of glass typically being 2 millimeters in thickness. The windshield is laminated in accordance with standard practices.

An electrically conductive and transparent coating, generally indicated at 26, is disposed between the plastic sheet 24 and one of the number two 16 and three 20 surfaces of the layers 12 and 18 of glass, but as illustrated, the coating 26 is disposed between the number two 16 surface of the outer layer 12 of glass and the plastic sheet 24. The layers 12 and 18 of glass and the plastic sheet 24 and the coating 26 are coextensive to define a windshield periphery. Such coatings 26 are now being applied to automotive glass as infrared filters or barriers to reduce solar heating of the vehicle interior. The coating 26, therefore, filters infrared light waves through substantially the entire area of the windshield, i.e., except special use areas to allow radio and/or infrared transmission, e.g., garage door opener space. The coating 26 may consist of sputtered or pyrolytic tin oxide, indium-tin oxide, silver-silver oxide or other metal oxide or metallic coatings in either single or multiple layers which exhibit the requisite optical characteristics. Many of these 1.R. films also provide excellent electrical conductivity which may be as low as 4–10 Ohms per square.

Figure 4:
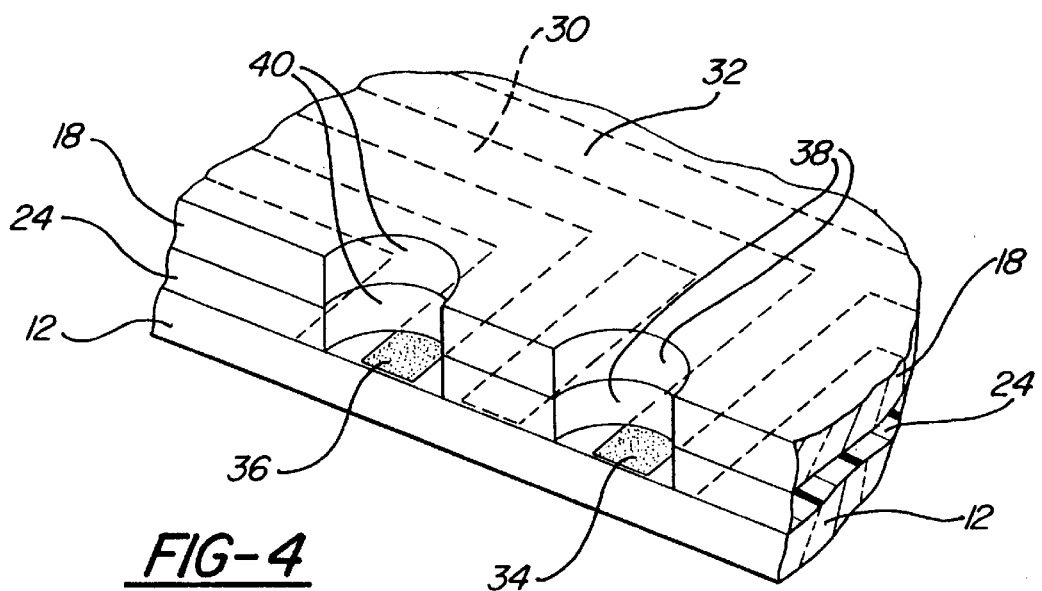
FIG. 4 is a fragmentary perspective view of another embodiment of the subject invention.
Figure 5:
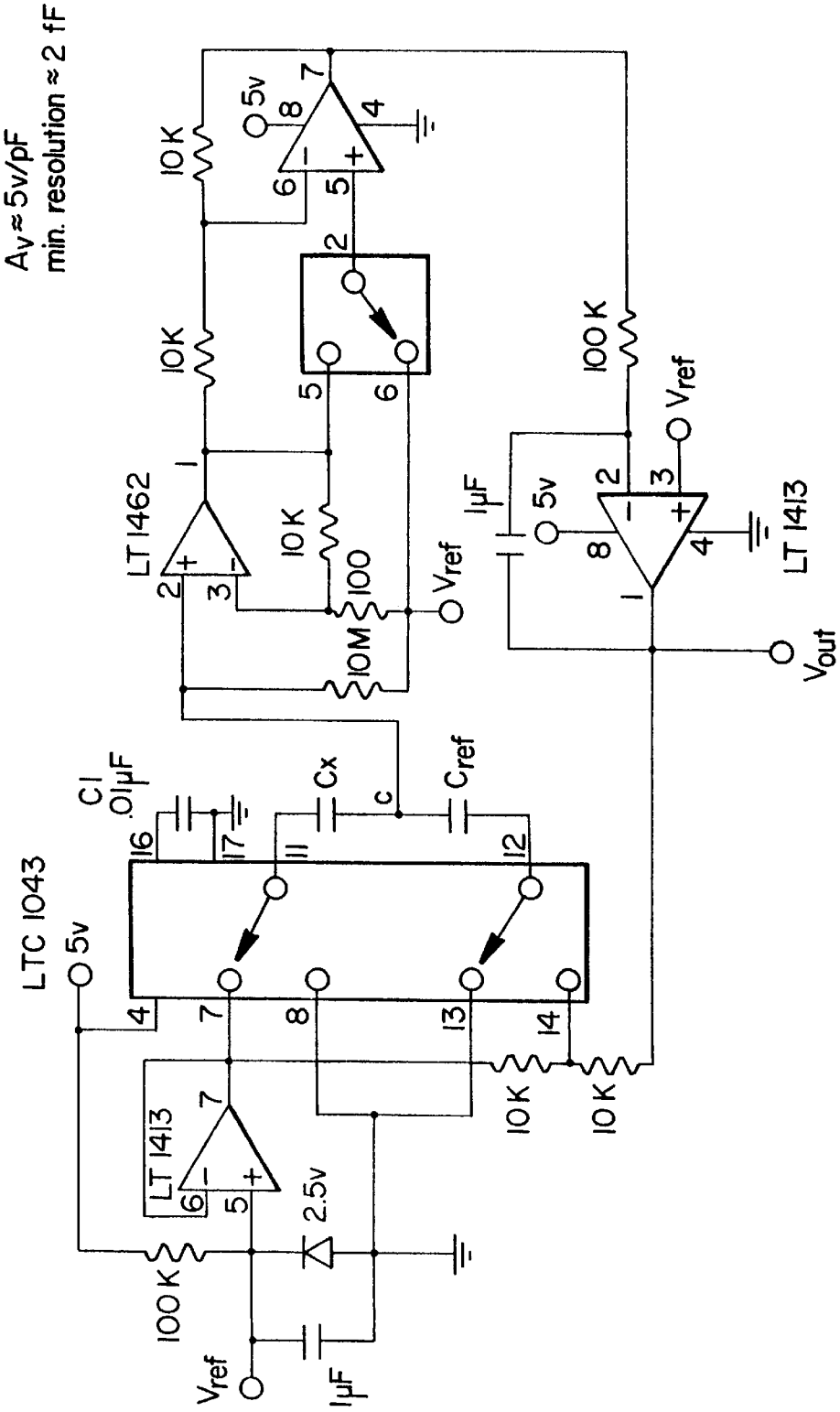
FIG. 5 is a circuit diagram of a known circuit which may be utilized with the subject invention.

Accordingly, the assembly 10 is characterized by an isolated section, generally indicated at 28, of the coating 26 being electrically separated from the remainder of the coating 26 for capacitively sensing the presence of moisture on the number one surface 14 of the outer layer 12 of glass. The isolated section 28 of the coating 26 comprises a first plurality of electrodes 30 and a second plurality of electrodes 32, the first 30 and second 32 plurality of electrodes being essentially parallel, interdigitized or interleaved and spaced from one another. As FIG. 4 is described above, it is from the opposite side of the assembly 10 from FIG. 2, whereby the inner layer 18 of glass is on top, which is to clearly illustrate the terminal or electrical contact 34 for the first plurality of electrodes 30 and the terminal or contact 36 for the first plurality of electrodes 32. These terminals 34 and 36 are electrically connected to the circuit illustrated in FIG. 5. In order to facilitate this direct coupling, cutouts 38 and 40 are made in the inner layer 18 of glass and the plastic sheet 24 for access, as shown in FIG. 4. Therefore, in one form of the invention, the sensing circuit illustrated in FIG. 5 is electrically coupled directly to the terminals 34 and 36 of the first 30 and second 32 plurality of electrodes. While a linear array of electrodes is shown, any interleaved electrode geometry would be suitable.

Figure 3:
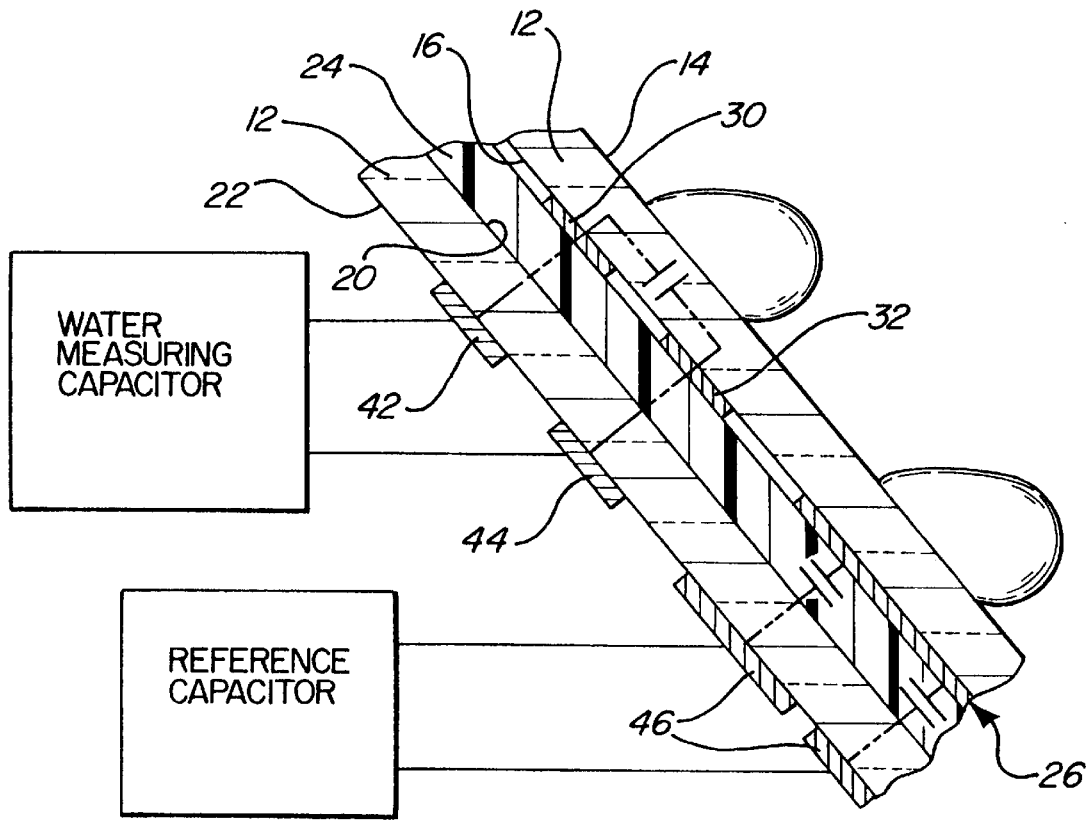
FIG. 3 is a fragmentary cross sectional view of one embodiment of the subject invention.

However, in an alternative form of the invention shown in FIG. 3, an indirect electrically coupling is utilized. More specifically, a first sensing plate or electrode 42 is disposed on the number four outer surface 22 of the inner layer 18 of glass for capacitive coupling with the first plurality of electrodes 30 through the inner layer 18 of glass and a second sensing plate or electrode 44 is disposed on the number four outer surface 22 of the inner layer 18 of glass for capacitive coupling with the second plurality of electrodes 32 through the inner layer 18 of glass. The circuit of Figure four is then electrically connected to the sensing plates or electrodes 42 and 44.

In order to eliminate the zero moisture capacitance effects upon the electrodes 30 and 32, e.g., thermal compensation and I or circuit normalization, a reference sensing capacitor 46 is disposed on the windshield for capacitive coupling with the remainder of the coating 26 for comparison with the capacitance of the first 30 and second 32 electrodes for isolating capacitive changes due to physical changes in the windshield from changes due to moisture on the number one surface of the outer layer 12 of glass. The reference sensing capacitor 46 is also disposed on the number four outer surface 22 of the inner layer 18 of glass.

Experimental sensors of $2 \times 10^4$ mm$^2$ have been tested, with little influence on vision through the glass. The necessary isolation of the capacitance sensing electrodes 30 and 32 has been accomplished by chemical photo etching, but in production the requisite isolation could be provided by laser scoring or simply by masking of the substrate (glass) prior to coating 26 deposition. Effective sensitivity of the capacitive sensor described herein is naturally compromised by the nominally 2 mm thick glass substrate which separates the water drops from the sensing electrodes 30 and 32. However, the dielectric constant of water, being nearly two orders of magnitude greater than air, permits an acceptable detection sensitivity to be realized for moderately large sensors ($10^4$ mm$^2$). That is, while the change in capacity per unit area of glass is admittedly small, the effect of many parallel changes in capacity due to a large number of raindrops can be substantial. Experimental data suggests that a sensor of $10^4$ mm$^2$ with a dry capacity of nominally 100 pF will show a change of 10 pF for a uniform distribution of 0.5 mm diameter droplets. A tangential sensitivity of 1 pF is considered to be optimal, and to that end a series of highly sensitive capacitance measuring circuits have been evaluated. The most successful of these circuits is shown in FIG.

5. The synchronous detection capacitance bridge shown in FIG. 5 was developed by Linear Technology, and is in the public domain, and variants of this circuit appear to be eminently useful as the front end for a sensitive capacitive rain sensor.

The invention also includes a method of fabricating a rain sensing windshield assembly 10 comprising the steps of sandwiching a sheet of transparent plastic 24 between and bonded to outer 12 and inner 18 layers of glass, as is well known in the art. Also well known, is the depositing of an electrically conductive and visibly transparent coating 26 between the sheet 24 and one of the layers 12 and 18 of glass be coextensive with the layers 12 and 18 of glass and the sheet 24 to define a windshield periphery.

The method is characterized by forming an isolated section 28 of the coating 26 electrically separated from the remainder of the coating 26 for capacitively sensing the presence of moisture on the outer layer 12 of glass. The forming of the isolated section 28 is specifically defined as forming a first plurality of electrodes 30 and a second plurality of electrodes 32 with the first 30 and second 32 plurality of electrodes being interdigitized or interleaved and spaced from one another.

The method may include disposing a first sensing plate 42 on the windshield for capacitive coupling with the first plurality of electrodes 30 and disposing a second sensing plate 44 on the windshield for capacitive coupling with the second plurality of electrodes 32. In addition, a reference sensing capacitor 46 may be disposed on the outer surface of the inner layer 18 of glass for capacitive coupling with the remainder of the coating 26 through the second layer of glass for comparison with the capacitance of the first 30 and second 32 electrodes for isolating capacitive changes due to physical changes in the windshield from changes due to moisture on the outer surface of the outer layer 12 of glass.

The sensing plates or electrodes 42, 44 and 46 are referred to as plates only to distinguish them from interior capacitor electrodes 30, 32. Plates 42, 44 and 46 perform as capacitor electrodes in their own right.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. A rain sensing windshield assembly comprising;
   an outer layer (12) of glass having a number one outer surface (14) and a number two interior surface (16), an inner layer (18) of glass having a number three inner surface (20) and a number four outer surface (22),
   a sheet of transparent plastic (24) sandwiched between and bonded to said number two (16) and three (20) surfaces of said layers (12 and 18) of glass,
   an electrically conductive and transparent coating (26) disposed between said sheet (24) and one of said number two (16) and three (20) surfaces of said layers (12 and 18) of glass,
   said layers (12 and 18) of glass and said sheet (24) and said coating (26) being coextensive to define a windshield periphery,
   said assembly characterized by an isolated section (28) of said coating (26) electrically separated from the remainder of said coating (26) for capacitively sensing the presence of moisture on said number one surface of said outer layer (12) of glass.

2. An assembly as set forth in claim 1 wherein said isolated section (28) of said coating (26) comprises a first plurality of electrodes (30) and a second plurality of electrodes (32), said first (30) and second (32) plurality of electrodes being interdigitized and spaced from one another.

3. An assembly as set forth in claim 2 including a first sensing plate (42) disposed on said number four outer surface (22) of said inner layer (18) of glass for capacitive coupling with said first plurality of electrodes (30) through said inner layer (18) of glass and a second sensing plate (44) disposed on said number four outer surface (22) of said inner layer (18) of glass for capacitive coupling with said second plurality of electrodes (32) through said inner layer (18) of glass.

4. An assembly as set forth in claim 2 wherein said coating (26) is disposed between said number two (16) surface of said outer layer (12) of glass and said sheet (24).

5. An assembly as set forth in claim 2 including a first sensing plate (42) disposed for capacitive coupling with said first plurality of electrodes (30) and a second sensing plate (44) for capacitive coupling with said second plurality of electrodes (32), a reference sensing capacitor (46) disposed on said windshield for capacitive coupling with said remainder of said coating (26) for comparison with the capacitance of said first (30) and second (32) electrodes for isolating capacitive changes due to physical changes in the windshield from changes due to moisture on said number one surface of said outer layer (12) of glass.

6. An assembly as set forth in claim 5 wherein said reference sensing capacitor (46) is disposed on said number four outer surface (22) of said inner layer (18) of glass.

7. An assembly as set forth in claim 6 including a first sensing plate (42) disposed on said number four outer surface (22) of said inner layer (18) of glass for capacitive coupling with said first plurality of electrodes (30) through said inner layer (18) of glass and a second sensing plate (44) disposed on said number four outer surface (22) of said inner layer (18) of glass for capacitive coupling with said second plurality of electrodes (32) through said inner layer (18) of glass.

8. An assembly as set forth in claim 2 wherein said coating (26) consists in part of a metal oxide.

9. An assembly as set forth in claim 8 wherein said sheet (24) consists of polyvinylbutyral.

10. An assembly as set forth in claim 9 wherein said coating (26) filters infrared light waves through substantially the entire area of said windshield except the etched area.

11. A method of fabricating a rain sensing windshield assembly comprising the steps of;
    sandwiching a sheet of transparent plastic (24) between and bonded to outer (12) and inner (18) layers of glass, and
    depositing an electrically conductive visibly and transparent coating (26) between the sheet (24) and one of the layers (12 and 18) of glass to be coextensive with the layers (12 and 18) of glass and the sheet (24) to define a windshield periphery,
    said method characterized by forming an isolated section (28) of the coating (26) electrically separated from the remainder of the coating (26) for capacitively sensing the presence of moisture on the outer layer (12) of glass.

12. A method as set forth in claim 11 wherein forming the isolated section (28) is further defined as forming a first plurality of electrodes (30) and a second plurality of electrodes (32) with the first (30) and second (32) plurality of electrodes being interdigitized and spaced from one another.

13. A method as set forth in claim 12 including disposing a first sensing plate (42) on the windshield for capacitive coupling with said first plurality of electrodes (30), disposing a second sensing plate (44) on the windshield for capacitive coupling with said second plurality of electrodes (32).

14. A method as set forth in claim 13 including disposing a reference sensing plate on the outer surface of the inner layer (18) of glass for capacitive coupling with the remainder of the coating (26) through the second layer of glass for comparison with the capacitance of the first (30) and second (32) electrodes for isolating capacitive changes due to physical changes in the windshield from changes due due to moisture on the outer surface of the outer layer (12) of glass.

* * * * *